US011052060B2

(12) United States Patent
Orndorff et al.

(10) Patent No.: US 11,052,060 B2
(45) Date of Patent: Jul. 6, 2021

(54) COMPOUNDS AND METHODS FOR TREATING AUTOIMMUNITY

(71) Applicants: ImmunoMolecular Therapeutics, INC., Woburn, MA (US); The Regents of the University of Colorado, a body corporate, Denver, CO (US)

(72) Inventors: Steve Orndorff, Broomfield, CO (US); Aaron Michels, Aurora, CO (US)

(73) Assignees: The Regents of the University of Colorado, a body corporate, Denver, CO (US); ImmunoMolecular Therapeutics, Inc., Woburn, MA (US)

( * ) Notice: Subject to any disclaimer, the term of this patent is extended or adjusted under 35 U.S.C. 154(b) by 0 days.

(21) Appl. No.: 16/357,397

(22) Filed: Mar. 19, 2019

(65) Prior Publication Data

US 2019/0262301 A1 Aug. 29, 2019

Related U.S. Application Data

(63) Continuation of application No. 15/894,118, filed on Feb. 12, 2018, now abandoned.

(51) Int. Cl.
| | | |
|---|---|---|
| *A61K 31/216* | (2006.01) |
| *A61K 45/06* | (2006.01) |
| *A61P 37/00* | (2006.01) |
| *A61P 3/10* | (2006.01) |
| *A61K 31/198* | (2006.01) |

(52) U.S. Cl.
CPC .......... *A61K 31/216* (2013.01); *A61K 31/198* (2013.01); *A61K 45/06* (2013.01); *A61P 3/10* (2018.01); *A61P 37/00* (2018.01)

(58) Field of Classification Search
CPC ..... A61K 31/216; A61K 31/198; A61K 45/06
See application file for complete search history.

(56) References Cited

U.S. PATENT DOCUMENTS

| | | | |
|---|---|---|---|
| 4,207,890 A | 6/1980 | Mamajek et al. |
| 4,434,153 A | 2/1984 | Urquhart et al. |
| 4,691,018 A | 9/1987 | Mori et al. |
| 4,735,804 A | 4/1988 | Caldwell et al. |
| 4,758,436 A | 7/1988 | Caldwell et al. |
| 4,767,627 A | 8/1988 | Caldwell et al. |
| 4,783,337 A | 11/1988 | Wong et al. |
| 5,415,994 A | 5/1995 | Imrich et al. |
| 5,424,193 A | 6/1995 | Pronovost et al. |
| 5,475,033 A | 12/1995 | Ohmori et al. |
| 5,594,100 A | 1/1997 | Wegman |
| 5,780,057 A | 7/1998 | Conte et al. |
| 5,939,281 A | 8/1999 | Lehmann et al. |
| 6,001,567 A | 12/1999 | Brow et al. |
| 6,207,197 B1 | 3/2001 | Illum et al. |
| 6,218,132 B1 | 4/2001 | Spack et al. |
| 7,144,569 B1 | 12/2006 | Anderson et al. |
| 7,749,503 B2 | 7/2010 | Tobia et al. |
| 8,053,197 B2 | 11/2011 | Vandenbark et al. |
| 8,314,210 B2 | 11/2012 | Wucherpfennig et al. |
| 9,629,848 B2 | 4/2017 | Eisenbarth et al. |
| 9,820,957 B2 | 11/2017 | Orndorff et al. |
| 2002/0150914 A1 | 10/2002 | Andersen et al. |
| 2003/0190665 A1 | 10/2003 | Vandenbark |
| 2004/0096734 A1 | 5/2004 | Calundann et al. |
| 2004/0137514 A1 | 7/2004 | Steenbakkers |
| 2004/0253276 A1 | 12/2004 | Sato et al. |
| 2004/0265327 A1 | 12/2004 | Grassetti et al. |
| 2005/0222270 A1 | 10/2005 | Olney et al. |
| 2006/0183670 A1 | 8/2006 | Orban |
| 2007/0021341 A1 | 1/2007 | Sela et al. |
| 2007/0196369 A1 | 8/2007 | Hoogenboom et al. |
| 2007/0243245 A1 | 10/2007 | Heinicke |
| 2008/0194462 A1 | 8/2008 | Wucherpfennig et al. |
| 2008/0214656 A1 | 9/2008 | Lim et al. |
| 2010/0172875 A1 | 7/2010 | Phan et al. |
| 2010/0172920 A1 | 7/2010 | Rottiers et al. |
| 2010/0233253 A1 | 9/2010 | Kavimandan et al. |
| 2011/0245334 A1 | 10/2011 | Du et al. |
| 2012/0171212 A1 | 7/2012 | Eisenbarth et al. |
| 2012/0195629 A1 | 8/2012 | Imai |
| 2013/0017262 A1 | 1/2013 | Mullen et al. |
| 2013/0115188 A1 | 5/2013 | Fritsche et al. |
| 2014/0050807 A1 | 2/2014 | Leighton |
| 2015/0010631 A1 | 1/2015 | Getts |
| 2018/0116988 A1 | 5/2018 | Anchordoquy et al. |
| 2018/0117124 A1 | 5/2018 | Michels et al. |

FOREIGN PATENT DOCUMENTS

| | | | |
|---|---|---|---|
| EP | 0098475 | 1/1984 | |
| JP | 49027860 B | * 7/1974 | ........... C07C 101/30 |
| JP | S49-027860 | 7/1974 | |
| JP | H04-069331 | 3/1992 | |
| JP | H09-52847 | 2/1997 | |
| WO | WO 84/02843 | 8/1984 | |
| WO | WO 94/01775 | 1/1994 | |
| WO | WO 94/29696 | 12/1994 | |
| WO | WO 99/67641 | 12/1999 | |
| WO | WO 00/38650 | 7/2000 | |
| WO | WO 00/39587 | 7/2000 | |
| WO | WO 01/64183 | 9/2001 | |
| WO | WO 03/070752 | 8/2003 | |
| WO | WO 2004/007528 | 1/2004 | |
| WO | WO 2004/110373 | 12/2004 | |
| WO | WO 2005/085323 | 9/2005 | |
| WO | WO 2010/141883 | 12/2010 | |
| WO | WO 2012/162697 | 11/2012 | |
| WO | WO 2016/191634 | 12/2016 | |

OTHER PUBLICATIONS

Valenta (Collection Czechoslovak Chem. Common., vol. 49, 1984, 1002-1008).*

(Continued)

*Primary Examiner* — Pancham Bakshi
(74) *Attorney, Agent, or Firm* — Sheridan Ross P.C.

(57) ABSTRACT

Compounds and compositions useful in methods of treating, ameliorating, or inhibiting the development of autoimmune diseases or Celiac disease by modulating the binding of DQ8 MHC class II molecules to antigenic peptides or fragments of antigenic peptides.

5 Claims, 7 Drawing Sheets

(56) References Cited

OTHER PUBLICATIONS

Cui (Chinese Journal of Organic Chemistry; 2008, vol. 28 (1), 78-83), with English abstract and compound.*
"Methyldopa Tablets USP," U.S. National Library of Medicine, [retrieved online from: dailymed.nlm.nih.gov/dailymed/fda/fdaDrugXsl.cfm?setid=916d802c-91b6-4015-9e57-7ebf7e9bb5ee&type=display].
"Prescribing Information for Methyldopa," AA Pharma Inc., Jul. 2010, 7 pages.
Michels "Targeting the Trimolecular Complex for Immune Intervention," ATDC 2014 Keystone Conference, Jul. 18, 2014, [retrieved online from: www.ucdenver.edu/academics/colleges/medicalschool/centers/BarbaraDavis/Documents/ATDC%202014%20Slides/3.4%20Michels%20Targeting%20Trimolecular%20Complex.pdf].
Sjoerdsma "Methyldopa," British Journal of Clinical Pharmacology, Jan. 1982, vol. 13, No. 1, pp. 45-49.
Trivedi et al. "Novel Gastro-Retentive Formulation for Methyldopa Using Hot Melt Extrusion (HME) Technology," AAPS, 2016, Poster No. 02W0300, 1 page.
Official Action for Canada Patent Application No. 2,980,940, dated Apr. 1, 2019 9 pages.
Corrected Notice of Allowance for U.S. Appl. No. 15/541,074, dated Apr. 26, 2019 2 pages.
Official Action for U.S. Appl. No. 15/934,790, dated Jul. 2, 2018 11 pages.
Official Action for U.S. Appl. No. 15/934,790, dated Sep. 4, 2019 20 pages.
Official Action for U.S. Appl. No. 15/556,710, dated May 31, 2019 13 pages.
U.S. Appl. No. 14/341,767, filed Jul. 26, 2014, Eisenbarth et al.
U.S. Appl. No. 15/355,738, filed Nov. 18, 2016, Eisenbarth et al.
U.S. Appl. No. 15/495,132, filed Apr. 24, 2017, Eisenbarth et al.
U.S. Appl. No. 15/817,739, filed Nov. 20, 2017, Orndorff et al.
U.S. Appl. No. 15/894,118, filed Feb. 12, 2018, Orndorff et al.
"T cell ELISpot Assays," ProImmune Ltd., Nov. 2013, 3 pages [retrieved online from: proimmune.com/ecommerce/page.php?page=elispot].
Aharoni et al., "Immunomodulation of experimental allergic encephalomyelitis by antibodies to the antigen-Ia complex," Nature, 1991, vol. 351, pp. 147-150.
ALDOMET® (Methyldopa), Merck & Co., Inc., Product Label, (NDA 13-400/S-086, 2004, pp. 3-8.
Ames et al., "Stereochemical Course In Vivo of Alpha-Methyldopa Decasrboxylation in Rat Brains," Biochem. Pharmacology, 1977, vol. 26(19), pp. 1757-1762.
Aoki et al., "NOD mice and autoimmunity," Autoimmun. Rev., 2005, vol. 4, pp. 373-379.
Au et al., "The Metabolism of 14C-Labelled 1-Methyldopa in Normal and Hypertensive Human Subjects," Biochem. J., 1972, vol. 129, pp. 1-10.
Auclair et al., "Comparative pharmacokinetics of D- and L-alphamethyldopa in plasma, aqueous humor, and cerebrospinal fluid in rabbits," Fundamental & Clinical Pharmacology, 1988, vol. 2(4), pp. 283-293.
Badiola et al. "Enantioselective Construction of Tetrasubstituted Stereogenic Carbons through Brønsted Base Catalyzed Michael Reactions: α'-Hydroxy Enones as Key Enoate Equivalent," Journal of the American Chemical Society, Dec. 2014, vol. 136, No. 51, pp. 17869-17881 (Abstract Only).
Boulard et al., "An interval tightly linked to but distinct from the h2 complex controls both overt diabetes (iddl6) and chronic experimental autoimmune thyroiditis (ceatl) in nonobese diabetic mice," Diabetes, 2002, vol. 51, pp. 2141-2147.
Bresson et al., "Moving towards efficient therapies in type 1 diabetes: To combine or not to combine?," Autoimmun Rev, 2007, vol. 6(5), pp. 315-322, 11 pages.

Chung et al., "Competitive Inhibition In Vivo and Skewing of the T Cell Repertoire of Antigen-Specific CTL Priming by an Anti-Peptide-MHC Monoclonal Antibody," J. Immunol., 2001, vol. 167, pp. 699-707.
Cochlovius et al.,"In Vitro and In Vivo Induction of a Th Cell Response Toward Peptides of the Melanoma-Associated Glycoprotein 100 Protein Selected by the TEPITOPE Program," J. Immunol., 2000, vol. 165, pp. 4731-4741.
Corper et al., "A structural framework for deciphering the link between I-Ag7 and autoimmune diabetes," Science, 2000, vol. 288, pp. 505-511.
Crawford et al., "Mimotopes for Alloreactive and Conventional T Cells in a Peptide-MHC Display Library," PLoS. Biol., 2004, vol. 2, p. 0523-0533.
Crawford et al., "Specificity and detection of insulin-reactive CDR+ T Cells in Type 1 diabetes in the nonobese diabetic (NOD) mouse," PNAS, 2011, vol. 108(40), pp. 16729-16734.
Czerkinsky et al., "Reverse ELISPOT assay for clonal analysis of cytokine production. I. Enumeration of gamma-interferon-secreting cells," Journal of Immunological Methods, 1988, vol. 110(1), pp. 29-36.
Daniel et al., "Prevention of type 1 diabetes in mice by tolerogenic vaccination with a strong agonist insulin mimetope," The Journal of Experimental Medicine, 2011, vol. 208(7), pp. 1501-1510.
Demuth et al., "Vaccine delivery with microneedle skin patches in nonhuman primates," Nat. Biotechnol. 2013, vol. 31(12), pp. 1082-1085.
Faideau et al., "Expression of preproinsulin-2 gene shapes the immune response to preproinsulin in normal mice," J. Immunol., 2004, vol. 172, pp. 25-33.
Fairbrother et al., "Effects of Three Plant Growth Regulators on the Immune Response of Young and Aged Deer Mice *Peromyscus maniculatus*," Arch. Environ. Contam, Toxicol., 1986, vol. 15, pp. 265-275.
Fife et al., "Insulin-induced remission in new-onset NOD mice is maintained by the PD-1-PD-L1 pathway," J. Experimental Med., 2006, vol. 203, pp. 2737-2747.
Fontenot et al., "Foxp3 programs the development and function of CD4+CD25+ regulatory T cells," Nature Immunology, 2003, vol. 4, pp. 330-336.
Fujisawa et al., "MHC-linked susceptibility to type 1 diabetes in the NOD mouse: further localization of 1dd16 by subcongenic analysis," Ann. NY Acad. Sci., 2006, vol. 1079, pp. 118-121.
Fukushima et al., "Combined insulin B:9-23 self-peptide and polyinosinic-polycytidylic acid accelerate insulitis but inhibit development of diabetes by increasing the proportion of CD4+Foxp3+ regulatory T cells in the islets in non-obese diabetic mice," Biochemical and Biophysical Research Communications, 2008, vol. 367, pp. 719-724.
Gillespie et al., "Clinical and Chemical Studies with a-Methyl-Dopa in Patents with Hypertension," Circulation, 1962, vol. 25, pp. 281-291.
Grigoriadis et al., "Alpha-Methyldopa-Induced Autoimmune Hemolytic Anemia in the Third Trimester of Pregnancy," Case Reports in Obstetrics and Gynecology, 2013, 2 pages, 2013:150278.
Hattori et al., "The NOD mouse: recessive diabetogenic gene within the major histocompatibility complex," Science, 1986, vol. 231, pp. 733-735.
Homann et al., "An immunologic homunculus for type 1 diabetes," J. Clin. Invest., 2006, vol. 116, pp. 1212-1215.
Hovhannisyan et al., "The role of HLA-DQ8 beta57 polymorphism in the anti-gluten T-cell response in coeliac disease," Nature, 2008, vol. 456, pp. 534-538.
Hurtenback, "Prevention of Autoimmune Diabetes in Non-Obese Diabetic Mice by Treatment with a Class II Major Histocompatibility Complex-blocking Peptide," Journal of Experimental Medicine, 1993, vol. 177(5), pp. 1499-1504.
Itoh et al., "Thymus and Autoimmunity: Production of CD25+ CD4+ Naturally Anergic and Suppressive T Cells as a Key Function of the Thymus in Maintaining Immunologic Self-Tolerance," J. Immnol. 1999, vol. 162, pp. 5317-5326.

(56) References Cited

OTHER PUBLICATIONS

Jasinski et al., "Transgenic Insulin (B:9-23) T-Cell Receptor Mice Develop Autoimmune Diabetes Dependent Upon RAG Genotype, H-2g7 Homozygosity, and Insulin 2 Gene Knockout," Diabetes, 2006, vol. 55, pp. 1978-1984.
Kachapati et al., "The Non-Obese Diabetic (NOD) Mouse as a Model of Human Type 1 Diabetes." Animal Models in Diabetes Research. Methods in Molecular Biology, 2012, vol. 933, pp. 3-16.
Kanagawa et al., "The role of I-Ag7 β chain in peptide binding and antigen recognition by T cells," Int Immunol., 1998, vol. 9, pp. 1523-1526.
Kmieciak et al. "Human T cells express CD25 and Foxp3 upon activation and exhibit effector/memory phenotypes without any regulatory/suppressor function," Journal of Translational Medicine, 2009, vol. 7, No. 89, 7 pages.
Kobayashi et al., "Conserved T cell receptor alpha-chain induces insulin autoantibodies," Proc. Natl. Acad. Sci. USA., 2008, vol. 105, pp. 10090-10094.
Lee et al., "Structure of a human insulin peptide-HLA-DQ8 complex and susceptibility to type 1 diabetes." Nature Immunology, 2001, vol. 2(6), pp. 501-507.
Leusch et al. "A short primer on benzene, toluene, ethylbenzene and xylenes (BTEX) in the environment and in hydraulic fracturing fluids," Griffith University, Nov. 17, 2010, 8 pages.
Levisetti et al., "The Insulin-Specific T Cells of Nonobese Diabetic Mice Recognize a Weak MHC-Binding Segment in More Than One Form," Journal of Immunology, 2007, vol. 178(10), pp. 6051-6057.
Levisetti et al., "Weak proinsulin peptide-major histocompatibility complexes are targeted in autoimmune diabetes in mice," Diabetes, 2008, vol. 57, pp. 1852-1860.
Li et al., A computer screening approach to immunoglobulin superfamily structures and interactions: Discovery of small non-peptidic CD4 inhibitors as novel immunotherapeutics, Proc. Natl. Acad. Sci. USA, 1997, vol. 94, pp. 73-78.
Maindonald "Experimental Design," Australian National University, Apr. 2013, 22 pages [retrieved online from: web.archive.org/web/20130411093944/https://maths-people.anu.edu.au/~johnm/planning/expdes.pdf].
Mareeva et al., "Antibody Specific for the Peptide-Major Histocompatibility Complex," J. Biol. Chem., 2004, vol. 279(43), pp. 44243-44249.
Masteller et al., "Peptide-MHC Class II Dimers as Therapeutics to Modulate Antige-Specific T Cell Responses in Autoimmune Diabetes," J. Immunol., 2003, vol. 171, pp. 5587-5595.
Merfeld et al., "The effect of pH and concentration on alphamethyldopa absorption in man," J Pharm Pharmacol., 1986, vol. 38, pp. 815-822.
Metrano et al. "Peptide-Catalyzed Conversion of Racemic Oxazol-5(4H)-ones into Enantiomerically Enriched α-Amino Acid Derivatives," The Journal of Organic Chemistry, Feb. 2014, vol. 79, No. 4, pp. 1542-1554.
Mordes et al., "Rat Models of Type 1 Diabetes: Genetics, Environment, and Autoimmunity," ILAR Journal, 2004, vol. 45, No. 3, pp. 278-291.
Moriyama et al., "Evidence for a primary islet autoantigen (preproinsulin 1) for insulitis and diabetes in the nonobese diabetic mouse," Proc. Nati Acad. Sci. USA, 2003, vol. 100, pp. 10376-10381.
Moseman et al., "Human Plasmacytoid Dendritic Cells Activated by CpG Oligodeoxynucleotides Induce the Generation of CD4+CD25+ Regulatory T Cells," The Journal of Immunology. 2004, vol. 173, pp. 4433-4442.
Nakayama et al., "Prime role for an insulin epitope in the development of type 1 diabetes in NOD mice," Nature, 2005, vol. 435(7039), pp. 220-223, author manuscript, 10 pages.
Nakayama et al., "Priming and effector dependence on insulin B:9-23 peptide in NOD islet autoimmunity," J. Clin. Invest., 2007, vol. 117, pp. 1835-1843.
Nakayama et al., "Regulatory vs. inflammatory cytokine T-cell responses to mutated insulin peptides in healthy and type 1 diabetic subjects," PNAS, 2015, vol. 112(14), pp. 4429-4434.

Oikonmakos et al., "Allosteric inhibition of glycogen phosphorylase alpha by the potential antidiabetic drug 3-isopropyl 4-(2-choropheny1)-1,4-dihydro-1-ethyl-2-methyl-pyridine-3,5,6-tricarboxylate," Protein Science, 1999, vol. 8, pp. 1930-1945.
Orban et al., "Autoantigen-specific regulatory T Cells induced in patients with Type 1 Diabetes Mellitus by Insulin B-chain immunotherapy," Journal of Autoimmunity, 2010, vol. 34(4), pp. 408-415, 21 pages.
Pietropaolo et al., "Primer: Immunity and Autoimmunity," Diabetes, 2008, vol. 57, pp. 2872-2882.
Puri et al., "Modulation of the Immune Response in Multiple Sclerosis," J. Immunol., 1997, vol. 158, pp. 2471-2476.
Renwick et al., "The Absorption and Conjugation of Methyldopa in Patients with Celiac and Crohn's Diseases During Treatment," Br. J. Clin. Pharmac., 1983, vol. 16, pp. 77-83.
Rosenblum et al., "Treating Human Autoimmunity: Current Practice and Future Prospects," Sci Transl Med, 2012, 4(125), 125sr1, pp. 1-20.
Sakaguchi et al., "Immunologic self-tolerance maintained by activated T cells expressing IL-2 receptor alpha-chains (CD25), Breakdown of a single mechanism of self-tolerance causes various autoimmune diseases," The Journal of Immunology, 1995, vol. 155(3), pp. 1151-1164c.
Salvati et al., "Recombinant human interleukin 10 suppresses gliadin dependent T cell activation in ex vivo cultured coeliac intestinal mucosa," Gut, 2005, retrieved from gut.bmj.com, retrieved on Aug. 21, 2012, vol. 54, pp. 46-53.
Savoie et al., "Use of BONSAI decision trees for the identification of potential MHC class I peptide epitope motifs," Pacific Symposium on Biocomputing, 1999, vol. 4, pp. 182-189, 8 pages.
Scheen, "Pathophysiology of type 2 diabetes," Acta Clinica Belgica, 2003, vol. 58(6), pp. 335-341.
Sharma et al. "Gastroretentive Drug Delivery System: An Approach to Enhance Gastric Retention For Prolonged Drug Release," International Journal of Pharmaceutical Sciences and Research, 2014, vol. 5(4), pp. 1095-1106.
Sjoerdsma et al., "Studies on the Metabolism and Mechanism of Action of Methyldopa," Circulation, 1963, vol. 28, pp. 492-502.
Sosinowski et al., "Type 1 diabetes: primary antigen/peptide/register/trimolecular complex," Immunologic Research, 2013, vol. 55, pp. 270-276.
Stadinski et al., "Diabetogenic T cells recognize insulin bound to IAg7 in an unexpected, weakly binding register," PNAS, 2010, vol. 107(24), pp. 10978-10983.
Stern et al., "Action of α-methyldopa on the intention tremor," Arzneinittel-Forschung, 1970, vol. 20(5), pp. 727-728.
Suri et al, "Natural peptides selected by diabetogenic DQ8 and murine I-A g7 molecules show common sequence specificity," The Journal of Clinical Investigation, 2005, vol. 115(8), pp. 2268-2276.
Suri et al., "The Murine Diabetogenic Class II Histocompatibility Molecule I-A (g7): Structural and Functional Properties and Specificity of Peptide Selection," Adv. Immunol., 2005, vol. 88, pp. 235-265.
Suri-Payer et al., "CD4+CD25+ T Cells Inhibit Both the Induction and Effector Function of Autoreactive T Cells and Represent a Unique Lineage of Immunoregulatory Cells" The Journal of Immunology, 1998, vol. 160, pp. 1212-1218.
Thomson et al., "FK 506: a novel immunosuppressant for treatment of autoimmune disease: Rationale and preliminary clinical experience," Springer Semin Immunopathol. 1993, vol. 14(4), 31 pages.
Todd et al., "A molecular basis for MHC class II associated autoimmunity," Science, 1988, vol. 240, pp. 1003-1009.
Vandenbark et al., "Treatment of multiple sclerosis with T-cell receptor peptides: Results of a double-blind pilot trial," Nature Medicine, 1996, vol. 2, pp. 1109-1115.
Wallis et al., "Type 1 Diabetes in the BB rat: A polygenic disease," Diabetes, 2009, vol. 58(4), pp. 1007-1017.
Wang et al., "Immunopharmacological and antitumor effects of second-generation immunomodulatory oligonucleotides containing synthetic CpR motifs," International Journal of Oncology, 2004, vol. 24, pp. 901-908.

(56) References Cited

OTHER PUBLICATIONS

Wicker et al., "Type 1 diabetes genes and pathways shared by humans and NOD mice," J. Autoimmun., 2005, vol. 25 (Suppl), pp. 29-33.
Wucherpfennig, "Insights into autoimmunity gained from structural analysis of MHC-peptide complexes," Current Opinion in Immunology, 2001, vol. 13, pp. 650-656.
Zhang et al., "Immunization with an insulin peptide-MHC complex to prevent type 1 diabetes of NOD mice," Diabetes Meta Res Rev, 2011, vol. 27, pp. 784-789.
Zhong et al., "Production, specificity, and functionality of monoclonal antibodies to specific peptide-major histocompatibility complex class II complexes formed by processing of exogenous protein," Proc. Natl. Acad. Sci. USA, 1997, vol. 94, pp. 13856-13861.
International Search Report and Written Opinion for International (PCT) Application No. PCT/US2016/013252, dated Mar. 30, 2016, 11 pages.
International Patentability Search Report for International (PCT) Application No. PCT/US2016/013252, dated Jul. 27, 2017, 10 pages.
Extended European Search Report for European Patent Application No. 16737819.9, dated Mar. 1, 2019, 7 pages.
International Search Report and Written Opinion for International (PCT) Application No. PCT/US2017/23571, dated Jul. 3, 2017, 17 pages.
International Search Report and Written Opinion for International (PCT) Application No. PCT/US2012/039849, dated Sep. 21, 2012, 9 pages.
International Preliminary Report on Patentability for International (PCT) Application No. PCT/US2012/039849, dated Dec. 5, 2013, 7 pages.
International Search Report and Written Opinion for International (PCT) Application No. PCT/US2016/034527, dated Aug. 25, 2016, 13 pages.
International Preliminary Report on Patentability for International (PCT) Patent Application No. PCT/US2016/034527, dated Dec. 7, 2017 12 pages.
Official Action for Canada Patent Application No. 2,980,940, dated Jul. 9, 2018 4 pages.
Extended European Search Report for European Patent Application No. 16800769.8, dated Jan. 8, 2019, 16 pages.
Official Action for U.S. Appl. No. 15/541,074, dated Apr. 16, 2018 5 pages, Restriction Requirement.
Official Action for U.S. Appl. No. 15/541,074, dated Aug. 28, 2018 10 pages.
Notice of Allowance for U.S. Appl. No. 15/541,074, dated Mar. 28, 2019, 5 pages.
Official Action for U.S. Appl. No. 15/466,026, dated May 17, 2017 24 pages.
Notice of Allowance for U.S. Appl. No. 15/466,026, dated Oct. 13, 2017 8 pages.
Official Action for U.S. Appl. No. 15/894,118, dated May 14, 2018 8 pages, Retriction Requirement.
Official Action for U.S. Appl. No. 15/894,118, dated Aug. 2, 2018 18 pages.
Notice of Allowance for U.S. Appl. No. 15/894,118, dated Dec. 6, 2018 10 pages.
Official Action for U.S. Appl. No. 14/119,926, dated May 21, 2015 6 pages, Restriction Requirement.
Official Action for U.S. Appl. No. 14/119,926, dated Nov. 3, 2015 19 pages.
Notice of Allowance for U.S. Appl. No. 14/119,926, dated Jul. 26, 2016 7 pages.
Notice of Allowance for U.S. Appl. No. 14/119,926, dated Aug. 19, 2016 5 pages.
Official Action for U.S. Appl. No. 15/556,710, dated Mar. 29, 2018 11 pages, Restriction Requirement.
Official Action for U.S. Appl. No. 15/556,710, dated Oct. 3, 2018 18 pages.
Official Action for U.S. Patent Application No. 17715858.1, dated Dec. 18, 2019 5 pages.
Official Action for Canada Patent Application No. 2,980,940, dated Dec. 11, 2019 3 pages.
Official Action for U.S. Appl. No. 15/556,710, dated Oct. 15, 2019 10 pages.
Official Action for U.S. Appl. No. 15/556,710, dated Mar. 4, 2020 11 pages.
Official Action for U.S. Appl. No. 15/934,790, dated Jun. 15, 2020 18 pages.
Official Action for European Patent Application No. 17715858.1, dated Jul. 27, 2020 3 pages.
Notice of Allowance for Canada Patent Application No. 2,980,940, dated Aug. 7, 2020 1 page.
Official Action for European Patent Application No. 16800769.8, dated Jul. 1, 2020 6 pages.

* cited by examiner

COMPOUNDS AND METHODS FOR TREATING AUTOIMMUNITY

CROSS REFERENCE TO RELATED APPLICATION

This application is a continuation of U.S. patent application Ser. No. 15/894,118, filed Feb. 12, 2018, which is incorporated herein by reference in its entirety.

TECHNICAL FIELD

This disclosure relates to the use of small organic molecules in the prevention or treatment of autoimmune diseases, such as autoimmune diabetes or Celiac disease.

BACKGROUND

Autoimmune disorders are diseases caused by the body producing an inappropriate immune response against its' own tissues, in which the immune system creates T lymphocytes and autoantibodies that attack one's own cells, tissues, and/or organs. Researchers have identified 80-100 different autoimmune diseases and suspect at least 40 additional diseases have an autoimmune basis.

Autoimmune disorders are classified into two types, organ-specific (directed mainly at one organ) and non-organ-specific (widely spread throughout the body). Examples of organ-specific autoimmune disorders are insulin-dependent Type 1 diabetes, which affects the pancreas; Celiac disease, which affects the lining of the small intestine; Hashimoto's thyroiditis and Graves' disease, which affect the thyroid gland; pernicious anemia, which affects the stomach, Addison's disease, which affects the adrenal glands; chronic active hepatitis, which affects the liver; and myasthenia gravis, which affects the muscles. Examples of non-organ-specific autoimmune disorders are rheumatoid arthritis, multiple sclerosis, and lupus.

One of the most prevalent organ-specific autoimmune diseases, Type 1 diabetes, is characterized by the production of autoantibodies that target the insulin-secreting pancreatic beta cells. The disease pathogenesis involves T cell infiltration into the islets of the pancreas, which subsequently destroys insulin producing beta cells, and results in overt symptoms of disease. In most cases, T cells can respond to an antigen only when the antigen is properly presented by an antigen-presenting cell expressing the appropriate major histocompatibility complex (MHC) molecule. Thus, T cell immune response to an antigen requires recognition by the T cell receptor of an antigen coupled to a MHC molecule, and this recognition requires the assembly of a tri-molecular complex between an antigen, a MHC molecule, and a T cell receptor.

Evidence strongly indicates that insulin/proinsulin is a primary auto-antigen in the development of type 1 diabetes in the non-obese diabetic (NOD) mouse model. Initial cloning of T cells from islets of NOD mice led to the discovery that the native insulin B chain amino acids 9-23 (B:9-23 insulin peptide) is the dominant antigenic peptide epitope presented by the class II MHC molecule I-A. Mice lacking the native B:9-23 sequence fail to develop diabetes and development of insulin autoantibodies and insulitis are markedly decreased. Restoring the native B:9-23 sequence with an islet transplant (but not bone marrow transplant) or peptide immunization, or a native proinsulin transgene, restores anti-insulin autoimmunity and generates CD4 T cells that cause diabetes.

The major genetic determinant of islet autoimmunity and diabetes in human and animal models are genes within the major histocompatibility complex, and in particular, class II MEW alleles. The NOD mouse's unique sequence of IA (homologous to human DQ) and lack of expression of I-E (shared with many standard mouse strains) are essential for the development of diabetes.

Celiac disease is an autoimmune disorder of the small intestine that affects between 1 in 100 and 1 in 300 people depending on the region of the world. The disease occurs in people of all ages and causes pain and discomfort in the digestive tract, chronic constipation and diarrhea, failure to thrive in children, anemia, and fatigue. The disease is caused by a reaction to gliadin, a prolamin (gluten protein) found in wheat and other common grains, such as barley and rye, in which the immune system cross-reacts with the small-bowel tissue, causing an inflammatory autoimmune reaction. The only known effective treatment is a lifelong gluten-free diet.

There exists a need in the art for safer and more effective methods for treating or slowing the progression or development of autoimmune disorders, such as autoimmune diabetes (type 1 diabetes, T1D) and Celiac disease (gluten sensitivity). This disclosure addresses these needs by providing molecules and formulations useful in the treatment and prevention of autoimmune diseases while achieving other advantages discussed more fully below.

SUMMARY

The present disclosure provides new compounds that may be used to prevent or reduce the binding of antigens to class II MHC molecules on antigen presenting cells thereby reducing or eliminating antigen presentation to T cells, as well as therapeutic uses of a compound of this disclosure and pharmaceutical compositions comprising a compound of this disclosure to prevent or slow the formation of autoimmune diabetes (type 1 diabetes; T1D) and Celiac disease in an individual.

Many autoimmune disorders have strong associations with specific HLA alleles, including T1D, which is the immune-mediated form of diabetes resulting from the chronic autoimmune destruction of pancreatic beta cells. Approximately 90% of all individuals with T1D have DQ8 and/or DQ2 alleles, with a predominance of DQ8 (DQA*0301, DQB*0302) in 50-60% of all T1D patients. DQ8 and DQ2 alleles confer significant disease risk while another DQ allele, DQ6 (DQB*0602), provides dominant protection from diabetes development. DQ8 and DQ2 are also the predominant HLA alleles in Celiac disease, present in about 99% of all Celiac disease patients. Thus, individuals with DQ8 and/or DQ2 alleles who have not yet manifested clinical disease may be at risk of developing T1D and/or Celiac disease, and/or may be suspected of suffering from T1D or Celiac disease.

T1D is now a predictable disease with the measurement of islet autoantibodies (insulin, glutamic acid decarboxylase, insulinoma associated antigen 2, and zinc transporter 8), but it cannot yet be prevented. Furthermore, T1D incidence is increasing 3-5% every year in industrialized countries with children less than five years of age being the most affected. Additionally, there is currently no known cure for T1D, and treatment for this disease consists of lifelong administration of insulin. Despite treatment with insulin therapy, long-term complications, including nephropathy, retinopathy, neuropathy, and cardiovascular disease can result. While the progress to complete insulin dependence occurs quickly after clinical onset, initially after diagnosis the pancreas is still able to produce a significant amount of insulin. The Diabetes Control and Complications Trial (DCCT) found that 20% of patients studied who were within 5 years of diagnosis, had remaining insulin production (0.2-0.5 pmol/ml). Thus, immunologic intervention during the window following diagnosis could save beta cell function, delay the onset of T1D, and reduce reliance on insulin administration.

Class II major histocompatability molecules are the primary susceptibility locus for many autoimmune diseases, including type 1 diabetes. "Diabetogenic" alleles HLA-DQ8 in humans and I-A$^{g7}$ in non-obese diabetic (NOD) mice confer disease risk, and both molecules share structural similarities. The present inventors have evaluated a novel pathway to identify safe and specific therapies to treat the underlying T cell autoimmunity in T1D. This pathway involves blocking allele-specific MHC class II antigen presentation as a treatment to inhibit DQ8-mediated T cell responses. DQ8 confers significant disease risk by presenting epitopes of insulin and other beta cell antigens to effector CD4 T cells. The present inventors have surprisingly found that the compounds of this disclosure block or reduce insulin and gliadin peptide presentation to T cells. Without intending to be bound by theory, it is believed that the compounds of this disclosure occupy a pocket along the DQ8 (DQA*03: 01, DQB*03:02) peptide binding groove, thereby blocking DQ8 restricted T cell responses in vitro, and inhibiting DQ8 antigen presentation in vivo. Blocking HLA-DQ8 antigen presentation in this way may help preserve beta cell mass (and endogenous insulin production) in new onset T1D and may also prevent or delay T1D onset in multiple islet autoantibody-positive individuals (i.e., 2 or more islet autoantibodies), 70-90% of whom develop diabetes within 10 years.

Thus, the present disclosure provides methods of preventing or reducing the binding of antigenic peptides to class II MHC molecules, to treat or slow the progression or development of T1D or Celiac disease in an individual suffering from, or at risk of developing, T1D or Celiac disease, comprising administering compounds of this disclosure to such individuals. The present disclosure also provides pharmaceutical compositions containing the compounds of this disclosure that are particularly useful in such methods of treating or slowing the progression or development of T1D.

One aspect of this disclosure is a method of inhibiting an autoimmune disease by administering to an individual in need of such treatment, a therapeutically effective amount of a compound of this disclosure that inhibits the T cell response to the targeted antigenic peptide of the autoimmune disease. These compounds inhibit the binding of an antigenic peptide to the DQ8 MHC class II molecule for presentation to CD4+ T cells, thereby slowing the development or progression of T1D or Celiac disease. The inhibition of the binding of an antigenic peptide to a DQ8 MHC class II molecule may result from a distortion of the spatial orientation of the complex so that the DQ8 MHC class II molecule-antigen complex is not properly presented to T cells, such that the trimolecular complex between 1) the MHC class II molecule on the surface of an antigen presenting cell, 2) the antigenic peptide, and 3) the CD4+ T cell, is not formed.

A related aspect provides a method of selectively treating T1D in an individual, including selecting an individual for treatment with a compound of this disclosure on the basis of the individual having at least two islet autoantibodies detectable in a blood sample from the individual, and selectively administering a compound of this disclosure to that individual.

In any of the methods of this disclosure, the individual may have been tested for the presence of autoantibodies to insulin or proteins within beta cells, wherein the presence of such antibodies in the individual is indicative of the presence or likely development of T1D. Thus, a related aspect of this disclosure provides methods of treating an individual found to have such autoantibodies by administering a compound of this disclosure to the individual.

Another aspect of this disclosure provides methods of monitoring and adjusting the dosage of a compound of this disclosure administered to an individual suffering from, or at risk of developing, an autoimmune disorder (such as T1D or Celiac disease) including receiving a blood sample from an individual suffering from, or at risk of developing, the autoimmune disorder who has been administered a compound of this disclosure and determining the DQ8-stimulated response of IL-2 T cells in the blood sample. The DQ8-stimulated response of IL-2 T cells in the blood sample is compared to a control level of DQ8-stimulated response of IL-2 T cells in blood samples from at least one of a patient suffering from the autoimmune disease and a control or 'wild type' individual known to be free of the autoimmune disease. The dosage and/or the frequency of the compound of this disclosure administered to the individual is increased if the DQ8-stimulated response of IL-2 T cells in the blood sample from the individual is statistically similar to the DQ8-stimulated response of IL-2 T cells from the baseline level in the T1D patient.

Other aspects of the invention will be set forth in the accompanying description of embodiments, which follows and will be apparent from the description. However, the following description of embodiments is given by way of illustration only, as various changes and modifications within the spirit and scope of the invention will become apparent to those skilled in the art and are encompassed within the scope of this disclosure.

DESCRIPTION OF EMBODIMENTS

Figure 1:
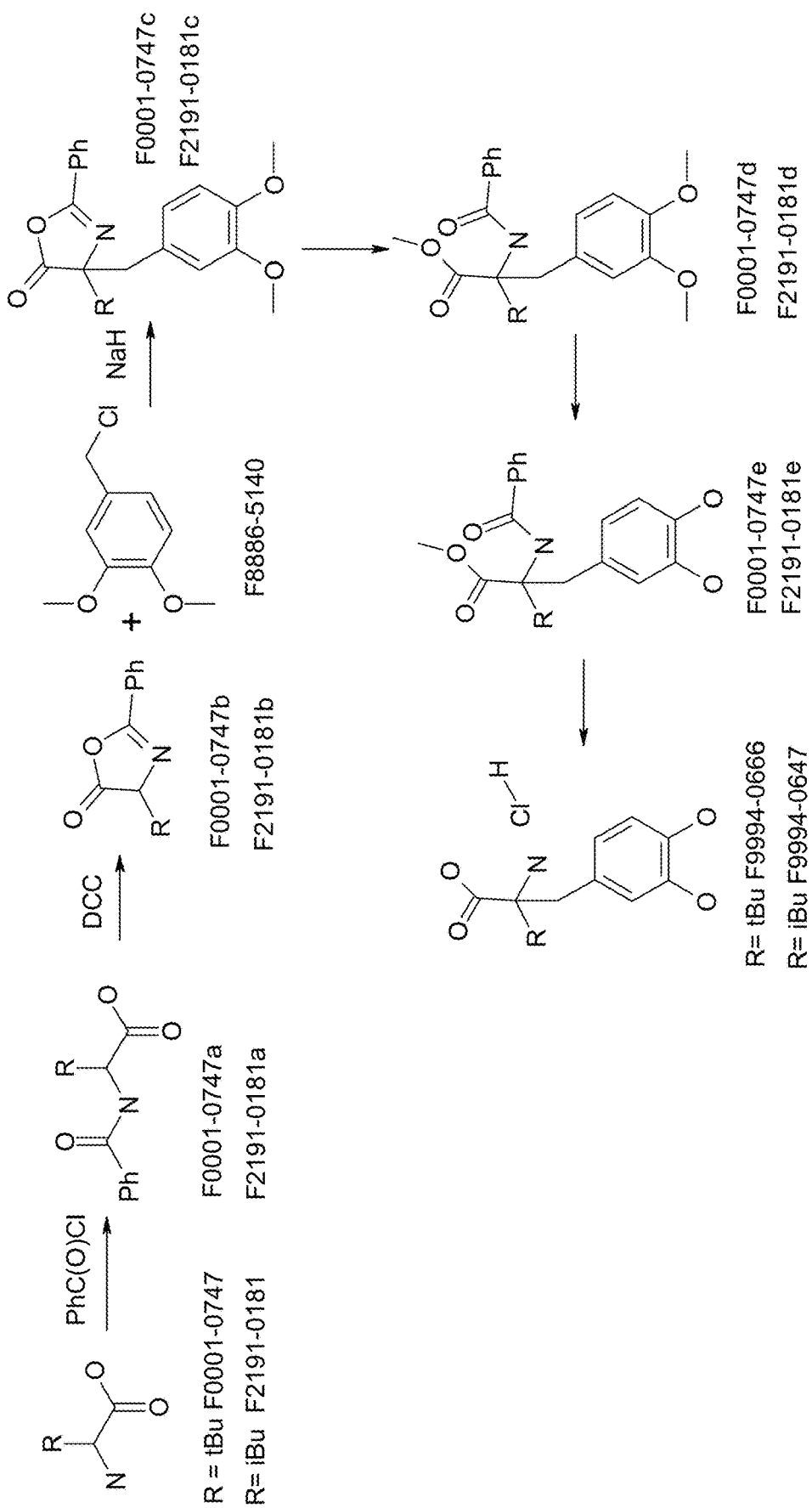
FIG. 1 shows a chemical synthesis scheme for methods of synthesizing compounds of this disclosure.

The present disclosure is drawn to methods of treating or slowing the progression or development of an autoimmune disease by reducing the binding, or altering the presentation of, antigenic peptides, or fragments of antigenic peptides, presented by an WIC class II molecule (DQ8) by the administration of a compound of this disclosure to an individual suffering from, or at risk of developing, an autoimmune disease such as autoimmune diabetes (type 1 diabetes; T1D) or Celiac disease.

Compounds of this Disclosure

As used herein, a compound of this disclosure includes a compound having a chemical structure according to Formula I and pharmaceutically acceptable enantiomers, tautomers, diastereomers, racemates, and salts thereof

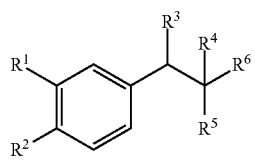

Formula I wherein:
$R^1$ is H, OH, $OR^7$, or $C_1$-$C_6$ alkyl;
$R^2$ is H, OH, $OR^7$, or $C_1$-$C_6$ alkyl;
$R^3$ is H, OH, or $OR^7$;
$R^4$ is H, $C_1$-$C_{10}$ alkyl, $C_1$-$C_{10}$ cycloalkyl; or $C_1$-$C_{10}$ alkyl fused to cycloalkyl or to aryl;
$R^5$ is H, $NR^8R^9$, or $C_1$-$C_6$ alkyl;
$R^6$ is H, $COOR^7$, $NR^8R^9$, or $CONR^8R^9$;
$R^7$ is H or $C_1$-$C_6$ alkyl; and,
$R^8$ and $R^9$ are independently H or $C_1$-$C_6$ alkyl.

Exemplary compounds of this disclosure include the compounds of Formula 1, wherein:
$R^1$ is OH;
$R^2$ is OH;
$R^3$ is H;
$R^4$ is $CH_2CH(CH_3)_2$, $CH_2C(CH_3)_3$, $CH_2$—$C_5H_9$, $CH_2$—$C_6H_{11}$, $CH_2$—$C_6H_5$;
$R^5$ is $NH_2$; and,
$R^6$ is H, COOH.

An exemplary compound of Formula I has the chemical structure:

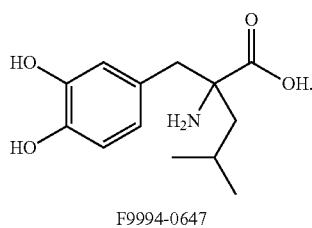 [SMILES: CC(C)CC(N)(Cc1ccc(O)c(O)c1)C(=O)O]

F9994-0647

Another exemplary compound of Formula I has the chemical structure:

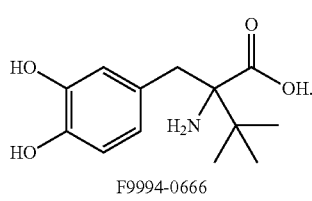 [SMILES: CC(C)(C)C(N)(Cc1ccc(O)c(O)c1)C(=O)O]

F9994-0666

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group".

Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like.

Exemplary substituents for radicals designated as "optionally substituted" include one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some embodiments of the present invention, alkyl groups are substituted with, for example, amino, or heterocycloalkyl, such as morpholine, piperazine, piperidine, azetidine, hydroxyl, methoxy, or a heteroaryl group, such as pyrrolidine.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl, or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member.

The terms "administration of a compound" or "administering a compound" refer to the act of providing a compound of the invention or pharmaceutical composition to a subject in need of treatment. Where two or more compounds are administered, co-administration is typically preferred with the co-administration being either via a combination formulation, or via parallel or subsequent administration of the two compounds. More typically, sequential co-administration will be performed such that the first compound is present in the patient's body in measurable quantities when the second compound is administered.

The term "solvate" refers to the compound formed by the interaction of a solvent and a compound. Suitable solvates are pharmaceutically acceptable solvates, such as hydrates, including monohydrates and hemi-hydrates.

The term "insulin peptide" is used to denote a peptide fragment of an insulin protein. Although the fragment is typically a subset of the amino acid sequence of the insulin protein, an insulin peptide may contain the entire amino acid sequence of a naturally-occurring insulin protein.

The terms "individual" or "subject" are used interchangeably herein. The terms "individual" and "individuals" refer to an animal, such as a mammal, including a non-primate (e.g., a cow, pig, horse, cat, dog, rat, and mouse) and a primate (e.g., a monkey such as a cynomolgous monkey, a chimpanzee), and a human. In certain embodiments, the subject is refractory or non-responsive to current treatments for an autoimmune disease.

"Tissue" means any biological sample taken from any individual, preferably a human. Tissues include blood, saliva, urine, biopsy samples, skin or buccal scrapings, and hair.

Persons of skill in the art will appreciate that blood plasma drug concentrations obtained in individual subjects will vary due to inter-patient variability in the many parameters affecting drug absorption, distribution, metabolism, and excretion. For this reason, unless otherwise indicated, when a drug plasma concentration is listed, the value listed is the calculated mean value based on values obtained from a group of subjects tested.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

The term "therapeutically-effective amount" of compounds of this disclosure means an amount effective to modulate the formation or progression of autoimmune diseases (including T1D and Celiac disease) in an individual.

The invention is based on the inventors' surprising discovery that certain compounds can reduce the presentation of antigenic peptides, or fragments of antigenic peptides, by WIC class II molecules in autoimmune diseases, such as T1D or Celiac disease.

Compounds of this disclosure may be formulated into pharmaceutical compositions using methods available in the art and provided in the appropriate pharmaceutical composition and administered by a suitable route of administration. The methods provided herein encompass administering pharmaceutical compositions containing compounds of this disclosure, if appropriate in the salt form, either used alone or in the form of a combination with one or more compatible and pharmaceutically acceptable carriers, such as diluents or adjuvants, or with another therapeutic agent. The second or additional therapeutic agent can be formulated or packaged with a compound of this disclosure. Of course, the second agent will only be formulated with a compound of this disclosure according to the judgment of those of skill in the art, as such co-formulation should not interfere with the activity of either agent or the method of administration. The compound of this disclosure and the second agent may be formulated separately. They may also be packaged together, or packaged separately, for the convenience of the medical practitioner. Exemplary additional agent(s) may include an anti-diabetic compound selected from at least one of an alpha-glucosidase inhibitor, a biguanide, a Dpp-4 inhibitor, a meglitinide, a sulfonylurea, a thiazolidinedione, or combinations of these agents.

In clinical practice a compound of this disclosure may be administered by any conventional route, in particular orally or parenterally. In preferred embodiments, a compound of this disclosure is administered orally, as solid or liquid compositions for oral administration, for example, as tablets, pills, hard gelatin capsules, powders or granules.

A composition provided herein is a pharmaceutical composition or a single unit dosage form. Pharmaceutical compositions and single unit dosage forms provided herein comprise a prophylactically or therapeutically effective amounts of a compound of this disclosure and typically one or more pharmaceutically acceptable carriers or excipients. In this context, the term "pharmaceutically acceptable" means approved by a regulatory agency of the federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Examples of suitable pharmaceutical carriers are described in "Remington's Pharmaceutical Sciences" by E. W. Martin.

A preferred formulation of this disclosure is a monophasic pharmaceutical composition suitable for oral administration for the treatment, prophylaxis, or slowing the progression of autoimmune diabetes, consisting essentially of a therapeutically-effective amount of a compound of this disclosure, and a pharmaceutically acceptable carrier.

Methods of Use

Provided herein are methods for the treatment and/or prophylaxis of an autoimmune disease in an individual. These methods include the treatment of an individual suffering from T1D or Celiac disease by the administration of an effective amount of a compound of this disclosure. These methods may encompass the step of administering to the individual in need of such treatment an amount of a compound of this disclosure effective for treating or delaying the development or progression of T1D or Celiac disease. The compounds of this disclosure that may be administered to an individual in these methods may be in the form of a pharmaceutical composition or single unit dosage form, as described above.

This disclosure includes methods of treating or slowing the progression or development of autoimmune diabetes (T1D) or Celiac disease by reducing or preventing the binding of WIC class II molecules to antigenic peptides or fragments of antigenic peptides of the autoimmune disease by the administration of a compound of this disclosure to individuals suffering from, or at risk of developing, T1D or Celiac disease.

A specific method includes treating T1D in an individual comprising administering an effective amount of a compound of this disclosure to an individual in need of such treatment. Another method includes treating Celiac disease in an individual comprising administering an effective amount of a compound of this disclosure to an individual in need of such treatment.

Another method provided herein includes treating an individual at risk of developing T1D by administering an effective amount of a compound of this disclosure to the individual. Another method includes treating an individual at risk of developing Celiac disease by administering an effective amount of a compound of this disclosure to the individual. Thus, this disclosure provides for the use of a compound of this disclosure in the manufacture of a medicament for the treatment of T1D, and the use of a compound of this disclosure in the manufacture of a medicament for the treatment of Celiac disease. This disclosure also provides a compound of this disclosure for use in the treatment of T1D, and a compound of this disclosure for use in the treatment of Celiac disease.

Exemplary compounds for use in these methods include a compound selected from the group consisting of compounds having the chemical structure:

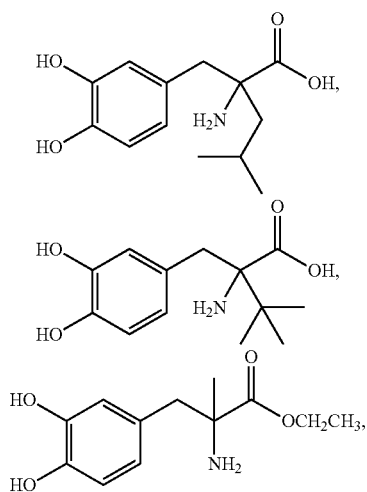

and
pharmaceutically acceptable enantiomers, tautomers, diastereomers, racemates, and salts thereof.

In these methods, a compound of this disclosure may be administered orally to the individual. The compound of this disclosure may be administered to an individual once daily, or more frequently. The compound of this disclosure may be administered to an individual as a pharmaceutically acceptable salt, solvate or hydrate thereof. The compound of this disclosure, or a pharmaceutically acceptable salt thereof, may be administered to an individual as a pharmaceutical composition described above.

In the methods of treating or slowing the progression or development of T1D of this disclosure, a compound of this disclosure or a pharmaceutically acceptable salt thereof, is administered to an individual suspected of suffering from, or at risk of developing T1D. Preferably, the administration to an individual diagnosed with T1D commences within 5 years of the initial diagnosis of T1D in the individual, or more preferably, within 1 year of the initial diagnosis of T1D in the individual, or more preferably, within 6 months of the initial diagnosis of T1D in the individual, or more preferably, within 1 month of the initial diagnosis of T1D in the individual.

In any of these methods, the individual may be administered a dosage of a compound of this disclosure, or a pharmaceutically acceptable salt, solvate or hydrate thereof, that is therapeutically effective to treat or delay the development or progression of T1D or Celiac disease in an individual.

In any of these methods, in addition to a compound of this disclosure, the individual may also be administered an anti-diabetic compound, including at least one of an alpha-glucosidase inhibitor, a biguanide, a Dpp-4 inhibitor, a meglitinide, a sulfonylurea, a thiazolidinedione, or combinations of these agents.

Another aspect of these methods includes an initial determination of which patients may benefit from the administration of a compound of this disclosure (and, optionally, an anti-diabetic compound, as described above), prior to administration of a compound of this disclosure to an individual determined to be in need of such treatment. As described above, DQ8 and DQ2 alleles confer significant risk of T1D and Celiac disease, while DQ6 allele provides dominant protection from diabetes development. Thus, individuals with DQ8 and/or DQ2 alleles are individuals at risk of developing T1D and/or Celiac disease. Additionally, individuals with islet autoantibodies (i.e., antibodies that specifically recognize insulin, glutamic acid decarboxylase, insulinoma associated antigen 2, or zinc transporter 8), or autoantibodies that recognize a MHC class II molecule bound to an insulin protein or to a gliadin peptide, or to insulin or gliadin peptide fragment(s), wherein the presence of such antibodies in the individual is indicative of the presence or likely development of T1D and/or Celiac disease in that individual. Such individual therefore may benefit from the methods of administering a compound of this disclosure, as described above.

The determination of which DQ8 or DQ2 alleles are present in an individual may enable a clinician to establish the subject's risk of developing an autoimmune disease.

For example, if the genotyping methods of this disclosure reveal a homozygous DQA*0301 or DQB*0302 genotype (two copies of one or both of these alleles) in the nucleic acid sample obtained from the individual, this finding indicates that the individual is more likely to develop T1D or Celiac disease. The clinician may then consider it beneficial to administer a compound of this disclosure in accordance with the methods of this disclosure. Additionally, an individual found to be heterozygous DQA*0301 or DQB*0302 genotype may still benefit from the administration of a compound of this disclosure. In this instance, the finding of a heterozygote genotype in the individual may be used to modify the dosage and/or dosing regimen of a compound of this disclosure to the individual, which may include reducing the dose or frequency of administration of a compound of this disclosure to the individual.

Alternatively, if the genotyping methods of this disclosure reveal homozygous wild type HLA alleles or protective alleles, such as DQB*0602, in the nucleic acid sample obtained from the individual, then the clinician may rule out an elevated risk of developing T1D or Celiac disease in the individual and consider different treatments or diagnoses for that individual.

A number of methods are available for analyzing and determining the DQ8 and/or DQ2 genotype in a subject, which can be applied to a nucleic acid sample obtained from a subject. Assays for detection of polymorphisms or mutations fall into several categories, including but not limited to, direct sequencing assays, fragment polymorphism assays, hybridization assays, and computer based data analysis. Protocols and kits or services for performing these general methods are commercially available and well known to those of skill in the art. In some embodiments, assays are performed in combination or in hybrid (e.g., different reagents or technologies from several assays are combined to yield one assay). Thus, the presence or absence of DQ8 and/or DQ2 alleles may be determined using direct sequencing. Alternatively or additionally, the DQ8 and/or DQ2 alleles may be determined using a PCR-based assay using oligonucleotide primers to amplify a DNA fragment containing the DQ8 and/or DQ2 polymorphism of interest. Alternatively or additionally, the DQ8 and/or DQ2 alleles may be determined using a fragment length polymorphism assay, such as a restriction fragment length polymorphism assay (RPLP), to detect a unique DNA banding pattern indicative of an DQ8 and/or DQ2 genotype based on cleaving the DNA at a series of positions is generated using an enzyme (e.g., a restriction endonuclease). Alternatively or additionally, the DQ8 and/or DQ2 alleles may be determined using a hybridization assay, wherein the genotype is determined based on the ability of the DNA from the sample to hybridize to a complementary DNA molecule (e.g., an oligonucleotide probe). The DQ8 and/or DQ2 polymorphisms of interest may be detected using a DNA chip hybridization assay, in which a series of oligonucleotide probes, designed to be unique to a given single nucleotide polymorphism, are affixed to a solid support, and the nucleic acid sample from the subject is contacted with the DNA "chip" and hybridization is detected. Alternatively or additionally, the DQ8 and/or DQ2 alleles may be determined using a "bead array" (such as those described in PCT Publications WO99/67641 and WO00/39587, each of which is herein incorporated by reference). Alternatively or additionally, the DQ8 and/or DQ2 alleles may be determined using an assay that detects hybridization by enzymatic cleavage of specific structures (such as those assays described in U.S. Pat. No. 6,001,567, and Olivier, M., The Invader assay for SNP Genotyping, 2005 Mutat. Res. 573 (1-2):103-10, both of which are incorporated herein by reference).

Genomic DNA samples are usually, but need not be, amplified before being analyzed. Genomic DNA can be obtained from any biological sample. Amplification of genomic DNA potentially containing an DQ8 and/or DQ2 polymorphism generates a single species of nucleic acid if the individual from whom the sample was obtained is homozygous at the polymorphic site, or two species of nucleic acid if the individual is heterozygous. RNA samples may also be subjected to amplification. In this case, amplification is typically, but not necessarily, proceeded by reverse transcription. Amplification of all expressed mRNA may also be performed (such as described in Innis M A et al., 1990, Academic Press, PCR Protocols: A Guide to Methods and Applications and Bustin SA 2000. Journal of Molecular Endocrinology, 25 Absolute quantification of mRNA using real-time reverse transcription polymerase chain reaction assays. pp. 169-193, which are hereby incorporated by reference in their entirety).

Any known method of analyzing a sample for an analyte can be used to practice the present invention, so long as the method detects the presence, absence, or amount of anti-islet antibodies. Examples of such methods include, but are not limited to, immunological detection assays and non-immunological methods (e.g., enzymatic detection assays). Additionally or alternatively, an binding compound is immobilized on a substrate, such as a microtiter dish well, a dipstick, an immunodot strip, or a lateral flow apparatus. A sample collected from a subject is applied to the substrate and incubated under conditions suitable (i.e., sufficient) to allow the formation of a complex between the binding compound and any anti-islet antibody present in the sample. Once formed, the complex is then detected. As used herein, the term "detecting complex formation" refers to identifying the presence of a binding compound complexed to an anti-islet antibody. If complexes are formed, the amount of complexes formed can, but need not be, quantified. Complex formation, or selective binding, between an anti-islet antibody and a binding compound can be measured (i.e., detected, determined) using a variety of methods standard in the art including, but not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BIACORE™ assay (e.g., using colloidal gold), an immunodot assay (e.g., CMG's Immunodot System, Fribourg, Switzerland), and an immunoblot assay (e.g., a western blot), an phosphorescence assay, a flow-through assay, a chromatography assay, a PAGE-based assay, a surface plasmon resonance assay, a spectrophotometric assay, a particulate-based assay, and an electronic sensory assay. The assays may be used to give qualitative or quantitative results. The assay results can be based on detecting the entire antibody or fragments, or degradation products. Some assays, such as agglutination, particulate separation, and immunoprecipitation, can be observed visually (e.g., either by eye or by a machine, such as a densitometer or spectrophotometer) without the need for a detectable marker. A detectable marker can be conjugated to the compound or reagent at a site that does not interfere with the ability of the compound to bind anti-islet antibodies. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label, a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin). Means of detecting such markers are well known to those of skill in the art.

A tri-molecular complex between an insulin or gliadin antigen, a MHC molecule, and T cell receptor can be detected by contacting a biological sample from an individual with an antibody specific for the complex, wherein the antibody is conjugated to a detectable marker. A detectable marker can also be conjugated to a tri-molecular complex between an insulin or gliadin antigen, a MHC molecule, and T cell receptor such that contact of the labeled complex with a biological sample from an individual can detect the presence of antibodies to the complex present in the individual tested. Detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin).

A tri-molecular complex may be detected by contacting the complex with an indicator molecule. Suitable indicator molecules include molecules that can bind to the tri-molecular binding molecule complex. As such, an indicator molecule can comprise, for example, an antibody. Preferred indicator molecules that are antibodies include, for example, antibodies reactive with the antibodies from animals in which the anti-islet antibodies are produced. An indicator molecule itself can be attached to a detectable marker of the present invention. For example, an antibody can be conjugated to biotin, horseradish peroxidase, alkaline phosphatase or fluorescein. One or more layers and/or types of secondary molecules or other binding molecules capable of detecting the presence of an indicator molecule may be used. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

A lateral flow assay may be used for detection, examples of which are described in U.S. Pat. Nos. 5,424,193; 5,415,994; WO 94/29696; and WO 94/01775 (all of which are incorporated by reference herein).

Once a biological sample from an individual has been analyzed to determine which allele of an DQ8 and/or DQ2 polymorphism is present, the individual can be selected, or identified, as likely or unlikely to develop, or at higher or lower risk of developing, T1D or Celiac disease. Such a selection is made using the results from the analysis step of the disclosed method. Those individuals selected as likely or at higher risk of developing T1D or Celiac disease may be treated with one or more compounds of this disclosure to treat or slow the development of the autoimmune disease in the individual.

Each publication or patent cited herein is incorporated herein by reference in its entirety. Additional objects, advantages, and novel features of this disclosure will become apparent to those skilled in the art upon examination of the following examples, which are not intended to be limiting.

EXAMPLES

Example 1

Synthesis of Compounds of this Disclosure

Figure 2:
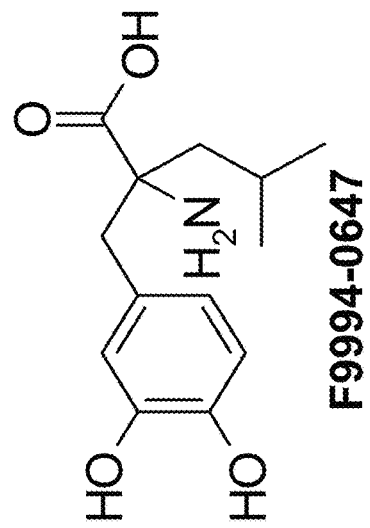
FIG. 2 shows the chemical structures of methyldopa and compounds synthesized using the synthesis methods depicted in FIG. 1.
Figure 2:
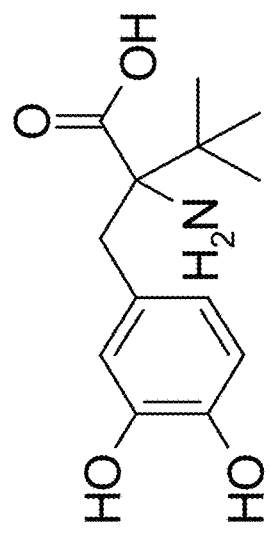
Figure 2:
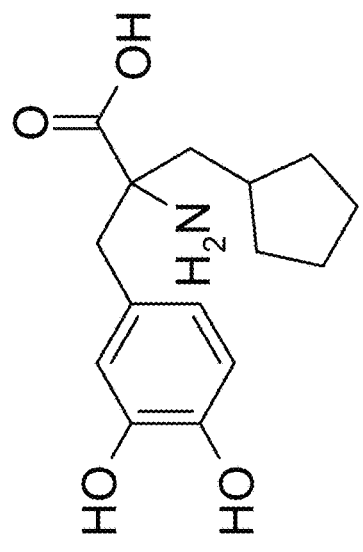
Figure 2:
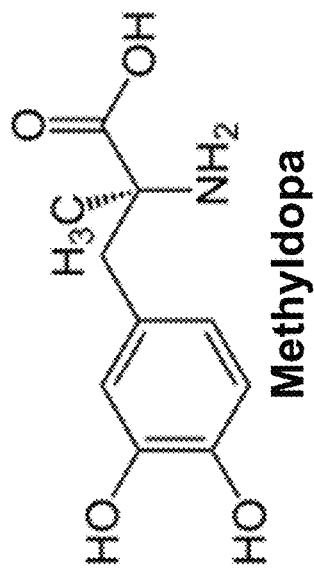
Figure 2:
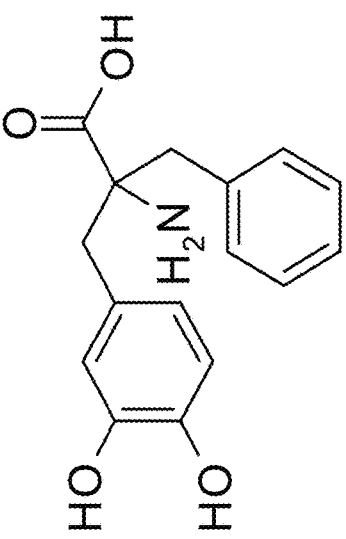
Figure 3A:
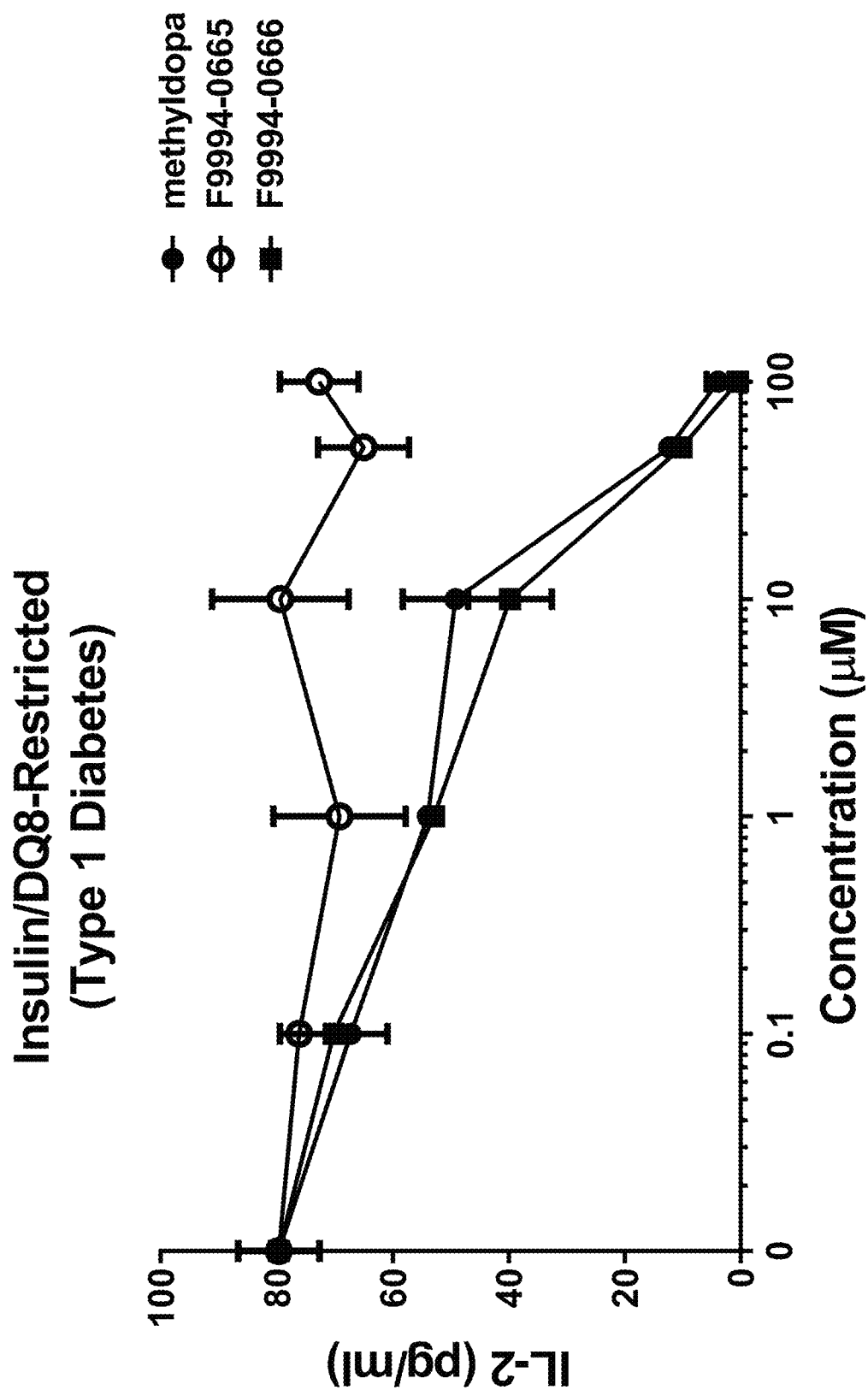
FIGS. 3A and 3B show concentration-dependent inhibition of an insulin-responsive CD4 T cell receptor (TCR) transductant (FIG. 3A) and gliadin-responsive CD4 TCR (FIG. 3B) by methyldopa (positive control), F994-0665, and F994-0666 (chemical structures shown in FIG. 2).
Figure 3B:
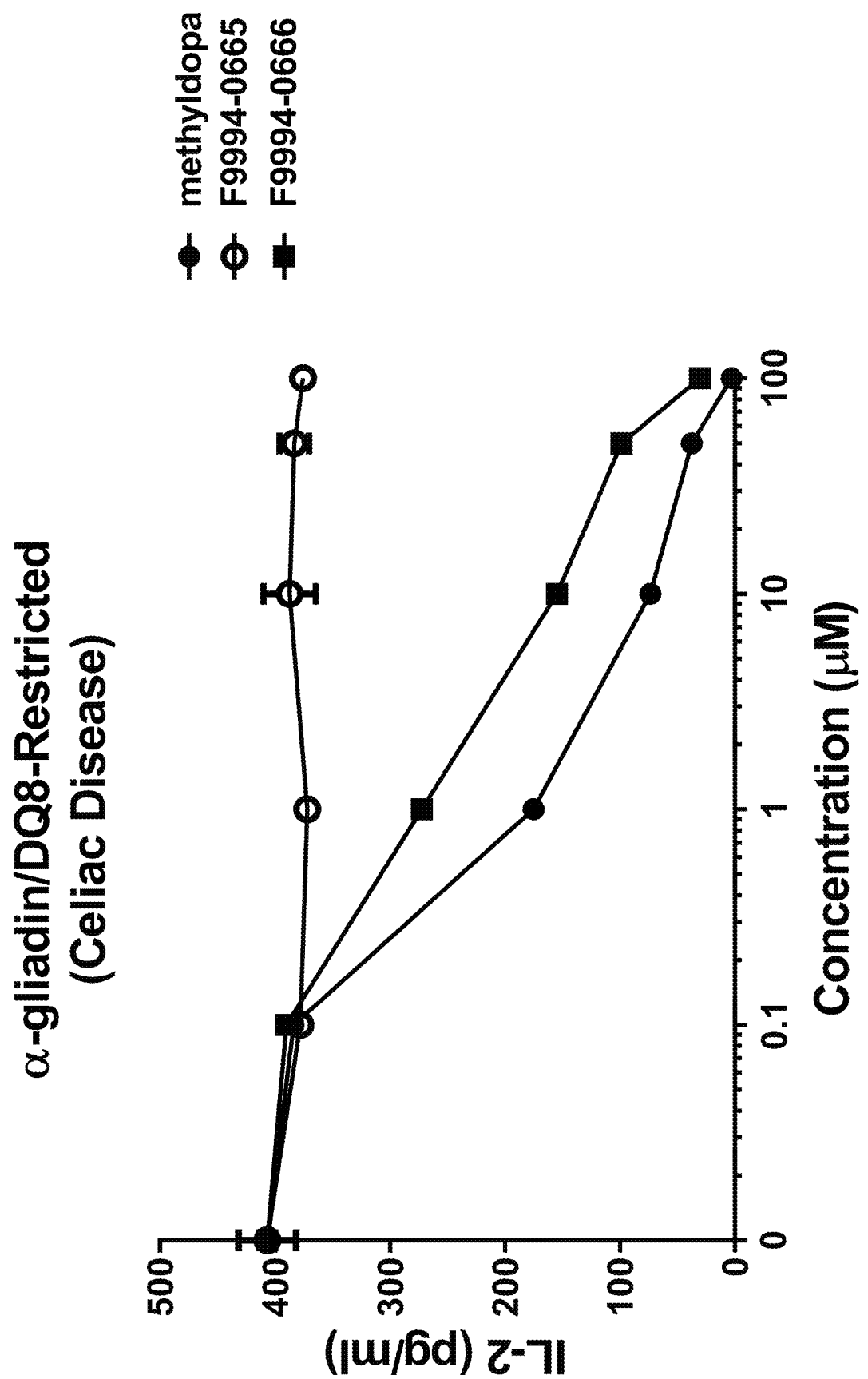
Figure 4A:
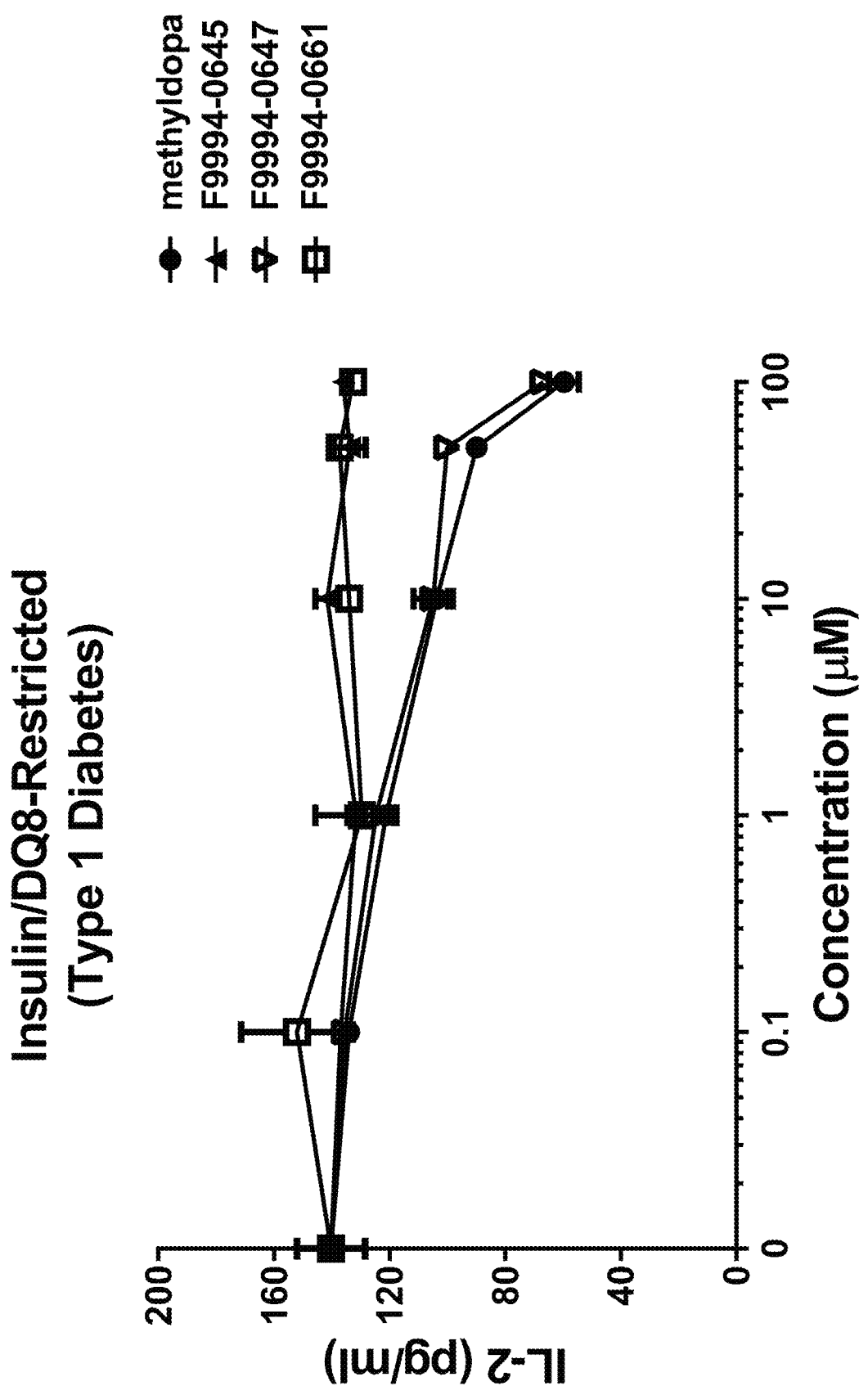
FIGS. 4A and 4B show concentration-dependent inhibition of an insulin-responsive CD4 TCR transductant (FIG. 4A) and gliadin-responsive CD4 TCR (FIG. 4B) by methyldopa (positive control), F994-0645, F994-0647, and F994-0661 (chemical structures shown in FIG. 2).
Figure 4B:
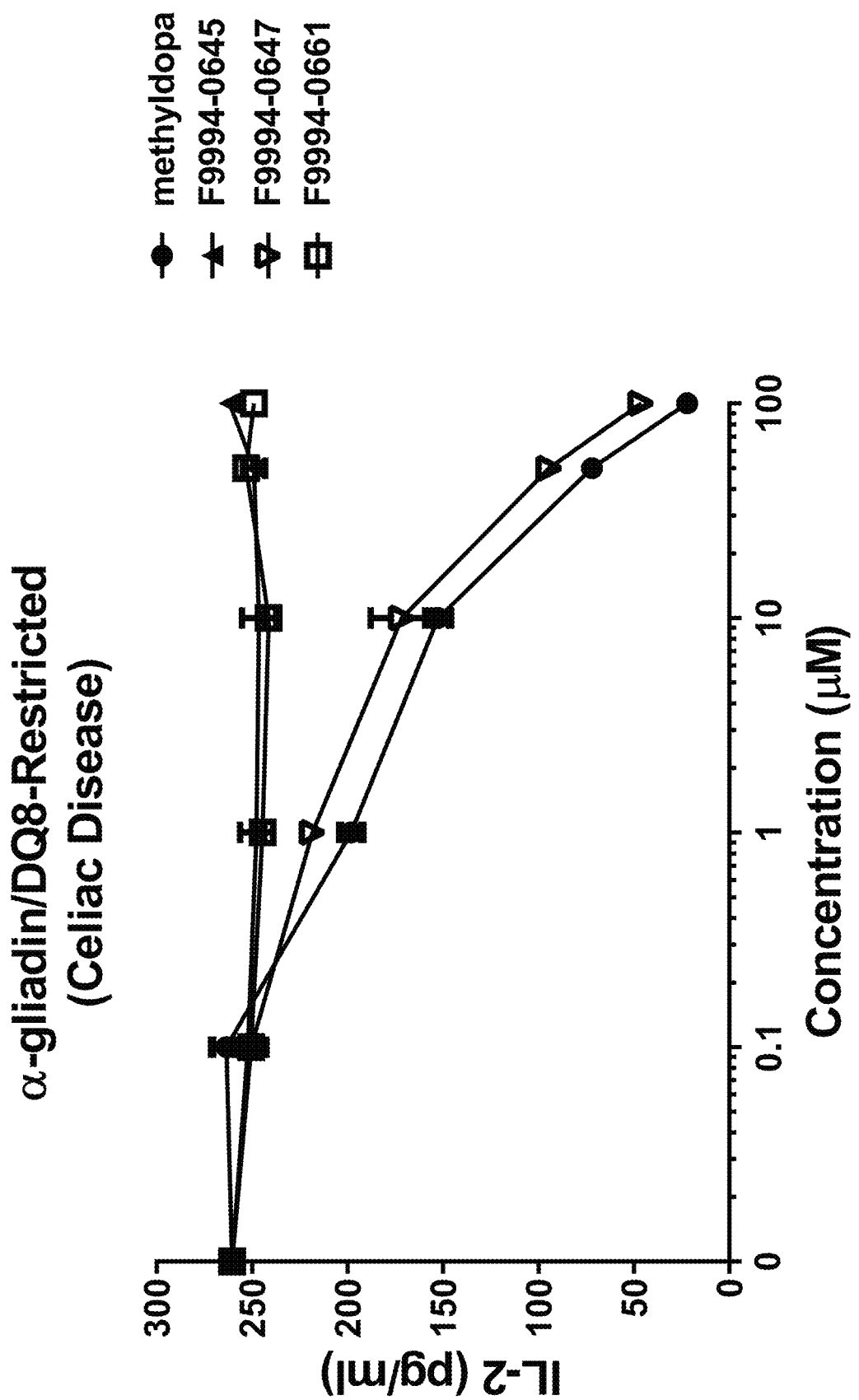

Compounds of this disclosure were synthesized by the following methods, which are described with reference to the chemical synthesis scheme depicted in FIG. and the chemical structures of the compounds synthesized shown in FIG. 2. Compounds F001-0747a and F2191-0181a were prepared according to published procedures (Journal of Organic Chemistry, 79(4):1542-54; 2014).

Compounds F001-0747b and F2191-0181b were prepared according to published procedures (Journal of the American Chemical Society, 136(51):17869-81; 2014). Yields were 70% and 75%, respectively.

Compounds F001-0747c/F2191-0181c: To a stirred solution of corresponding compound F001-0747b or F2191-0181b, oxazolone (25.8 mmol) and F8886-5140 (7.22 g, 38.7 mmol) in DMF (75 ml) was added under argon and ice-bath cooling 1.24 g 60% NaH (31 mmol) in small portions (temperature less than 10-15 C). The mixture was stirred for 30 min at 10-15 C and for 12 hrs at room temperature and then poured onto ice (150 g), with aq. HCl, and $Et_2O$ (2×150 ml), the organic phase washed with brine (2×100 ml), dried ($Na_2SO_4$), and evaporated. The product was purified by preparative column chromatography ($SiO_2$, EtOAc/Hexane (fraction 2) then final purification EtOAc/Hex—1:9). Yields 30/27%.

Compounds F001-0747d and F2191-0181d: Na (400 mg, 17.1 mmol) was dissolved in 30 mL of dry MeOH, and then substrate F001-0747c or F2191-0181c (11.4 mmol) was added in 20 ml of MeOH and the resulting mixture was stirred at room temperature for 16 hours. The reaction mixture was evaporated to dryness, the residue was diluted with water and acidified to pH greater than 7 (HCl), and the product was extracted with $Et_2O$ (2×50) and washed with $H_2O$ (2×50). The organic layer was dried over $Na_2SO_4$, filtered and evaporated/dried in vacuo. Yields were 82% and 70%, respectively.

Compounds F001-0747e and F2191-0181e: $BBr_3$ (2.25 g, 9 mmol) was added in one portion to a stirred solution of F001-0747d or F2191-0181d (1.8 mmol) in freshly distilled $CH_2Cl_2$ (20 ml) under argon at −60 C. The solution was stirred for 16 hrs at room temperature and poured into saturated aqueous $NH_4C_1$ solution (50 ml), and $CH_2Cl_2$ (50 ml). The aqueous layer was extracted with DCM (2×25 ml). The combined organic layers were dried over $Na_2SO_4$, filtered and evaporated in vacuo. Yields were 68% and 74%, respectively.

Compounds F9994-0666 and F9994-0649: A solution of F001-0747e or F2191-0181e (0.5 mmol) in aqueous HCl (37%, 5 ml) was stirred under reflux for 16 hours. The solution was separated from oil stuck to the flask and washed with EtOAc (3×10 ml). The aqueous solution was evaporated in vacuo. The residue was dissolved in water (10 ml), the solution was washed with EtOAc (2×10 ml) and $Et_2O$ (2×10 ml). The aqueous layer was evaporated in and dried in vacuo to give the target compounds F9994-0666 and F9994-0649 in 42% and 53% yield, respectively.

Example 2

Compounds of this Disclosure Inhibit DQ8 Restricted T Cell Responses In Vitro

Inhibition of DQ8 antigen presentation by compounds of this disclosure was tested and compared in vitro. HLA-DQ8 antigen presenting cells were cultured with a fixed concentration of peptide and a concentration of one of the tested compounds for 4 hours. TCR transductants were then added to each culture condition and cultured overnight. Secreted IL-2 from the TCR transductant was measured by ELISA for each condition.

As shown in FIGS. 3-6, gliadin-responsive CD4 T cell receptor (TCR) or insulin-responsive CD4 TCR transductants were blocked in a dose-dependent manner with statistically similar $IC_{50}$ values between the tested compounds. In these figures, 0 represents the TCR transductant response to peptide without the addition of the test compound. No antigen IL-2 responses (negative control) were very low at less than 2 pg/ml (results are presented as mean+/−SEM). These data demonstrate the dose-dependent inhibitory effects of the tested compounds of this disclosure on DQ8 antigen presentation in in vitro models of Celiac disease and T1D.

Example 3

Structure Activity Relationship for Compounds that Inhibit MHC-Antigen Binding

Figure 5:
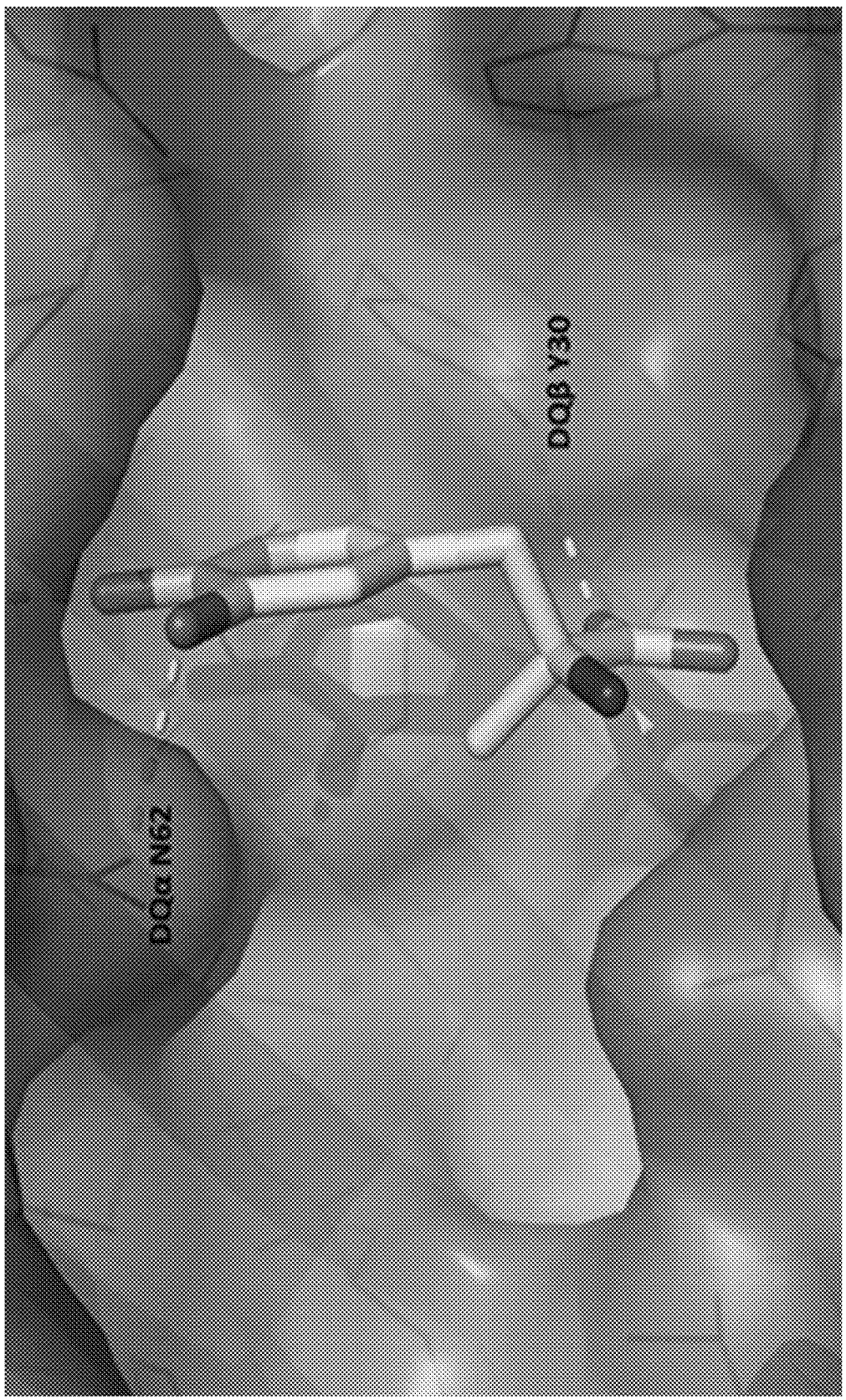
FIG. 5 shows a molecular docking model of methyldopa in the DQ8 WIC II antigen-binding cleft.

Using the crystal structure of DQ8, methyldopa was modeled interacting with amino acid residues of the DQ8 alpha and beta chains within the antigen-binding cleft (FIG. 5). Two hydrogen bonds (FIG. 5, dashed lines) are predicted between methyldopa and DQ8 amino acid side chains. Testing structurally related compounds indicated that the modeled hydrogen bonds were indeed important to inhibit a T cell response, as removal of a hydroxyl group on the benzene ring or removal of the carboxylic acid abrogated the response (SAR table, below). Further insights from these structure activity relationships indicate that a hydroxyl group on the benzene ring is a hydrogen bond donor to DQα62 asparagine and the carboxylic acid is a hydrogen bond acceptor for DQβ30 tyrosine (FIG. 5).

TABLE

Structure Activity Relationships for Methyldopa

| Chemical Structure and Name* | Clone 5 IC$_{50}$ (insulin/ DQ8) | 489 IC$_{50}$ (α-gliadin/ DQ8) |
|---|---|---|
| 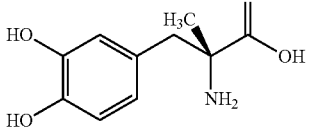<br>α-methyldopa,<br>2-amino-3-(3,4-dihydroxyphenyl)-2-methylpropanoic acid | 3.4 μM | 17.7 μM |
| 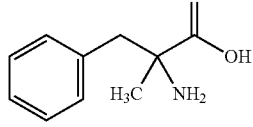<br>α-methylphenylalanine,<br>2-amino-2-methyl-3-phenylpropanoic acid | No inhibition | No inhibition |
| 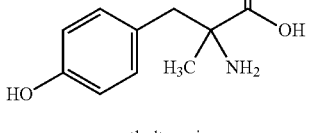<br>α-methyltyrosine,<br>2-amino-3-(4-hydroxyphenyl)-2-methylpropanoic acid | No inhibition | No inhibition |
| 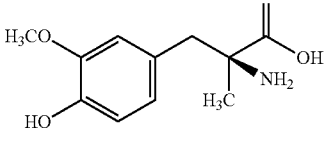<br>3-O-methyl methyldopa,<br>2-amino-3-(4-hydroxy-3-methoxyphenyl)propanoic acid | No inhibition | No inhibition |
| 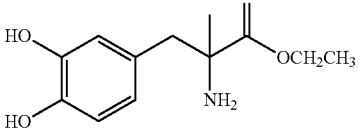<br>α-methyldopa ethyl ester,<br>Ethyl-2-amino-3-(3,4 dihydroxyphenyl)-2-methylpropanoate | 5.8 μM | 7.8 μM |
| 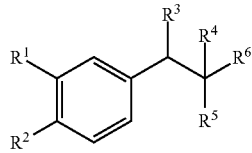<br>α-methylnorepinephrine,<br>4-(2-amino-1-hydroxypropyl)benzene-1,2-diol | No inhibition | No inhibition |

*Common chemical name followed by International Union of Pure and Applied Chemistry (IUPAC) name.

It will be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification refers to at least one of something selected from the group consisting of A, B, C . . . and N, the text should be interpreted as requiring only one element from the group, not A plus N, or B plus N, etc.

What is claimed is:

1. A compound having a structure according to Formula I and pharmaceutically acceptable enantiomers, tautomers, diastereomers, racemates, and salts thereof

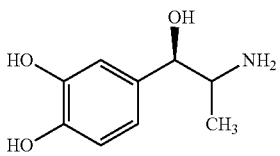

Formula I wherein:
R$^1$ is OH, OR$^7$, or C$_1$-C$_6$ alkyl;
R$^2$ is OH, OR$^7$, or C$_1$-C$_6$ alkyl;
R$^3$ is H, OH, or OR$^7$;
R$^4$ is CH$_2$—C$_5$H$_9$, or CH$_2$C$_6$H$_{11}$;
R$^5$ is H, NR$^8$R$^9$, or C$_1$-C$_6$ alkyl;
R$^6$ is all COOR$^7$, or CONR$^8$R$^9$;
R$^7$ is H or C$_1$-C$_6$ alkyl; and,
R$^8$ and R$^9$ are independently H or C$_1$-C$_6$ alkyl.

2. A pharmaceutical composition comprising a compound of claim 1 in combination with a pharmaceutically acceptable carrier.

3. The pharmaceutical composition of claim 2, wherein the composition is formulated for oral or parenteral administration.

4. The pharmaceutical composition of claim 3, wherein the composition is formulated for a single unit dosage form.

5. The pharmaceutical composition of claim 3, wherein the composition is formulated as a monophasic dosage form.

* * * * *